(12) United States Patent
Guidotti et al.

(10) Patent No.: US 6,429,351 B1
(45) Date of Patent: *Aug. 6, 2002

(54) ABSORBENT BODIES IN ABSORBENT ARTICLES HAVING IMPROVED LIQUID ACQUISITION PROPERTIES

(75) Inventors: Ted Guidotti; Anette Buschka, both of Göteborg; Anders Gustafsson, Billdal; Urban Widlund, Pixbo, all of (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,454

(22) PCT Filed: Jun. 26, 1997

(86) PCT No.: PCT/SE97/01152

§ 371 (c)(1),
(2), (4) Date: Dec. 15, 1998

(87) PCT Pub. No.: WO98/00081

PCT Pub. Date: Jan. 8, 1998

(30) Foreign Application Priority Data

Jun. 28, 1996 (SE) ................................................ 9602579

(51) Int. Cl.[7] .............................................. A61F 13/15
(52) U.S. Cl. ................................. 604/378; 604/385.01
(58) Field of Search ....................... 604/385.01, 385.12, 604/385.101, 385.16, 385.23, 352, 369, 378, 367, 379, 380, 383, 385.21, 389, 391, 368

(56) References Cited

U.S. PATENT DOCUMENTS

| | | |
|---|---|---|
| 3,889,679 A | 6/1975 | Taylor |
| 4,027,672 A | 6/1977 | Karami |
| 4,333,462 A | 6/1982 | Holtman et al. |
| 4,333,463 A | 6/1982 | Holtman |
| 4,333,464 A | 6/1982 | Nakano |
| 4,413,996 A | 11/1983 | Taylor |
| 4,560,372 A | 12/1985 | Pieniak |
| 4,643,727 A | 2/1987 | Rosenbaum |
| 5,433,715 A | * 7/1995 | Tanzer et al. ................ 604/368 |
| 5,658,269 A | * 8/1997 | Osborn, III et al. ..... 604/385.2 |
| 5,674,212 A | * 10/1997 | Osborn, III et al. ..... 604/385.1 |
| 5,683,375 A | * 11/1997 | Osborn, III et al. ..... 604/385.2 |
| 5,702,382 A | * 12/1997 | Osborn, III et al. ..... 604/385.2 |
| 5,788,684 A | * 8/1998 | Abuti et al. ................. 604/368 |
| 5,797,892 A | * 8/1998 | Glaug et al. ................. 604/361 |
| 5,824,004 A | * 10/1998 | Osborn, III et al. ..... 604/385.2 |
| 5,830,202 A | * 11/1998 | Bogdanski et al. .......... 604/378 |
| 5,855,572 A | * 1/1999 | Schmidt ..................... 604/378 |
| 5,868,724 A | * 2/1999 | Dierckes, Jr. et al. ....... 604/368 |
| 5,895,379 A | * 4/1999 | Litchholt et al. ........... 604/378 |
| 5,941,863 A | * 8/1999 | Guidotti et al. ............. 604/378 |
| 5,961,507 A | * 10/1999 | Widlund ..................... 604/378 |

FOREIGN PATENT DOCUMENTS

| | | |
|---|---|---|
| EP | 0124365 B1 | 11/1984 |
| EP | 0528567 B1 | 2/1993 |
| GB | 2156681 B | 10/1985 |
| WO | WO 87/01914 | 4/1987 |
| WO | 0393953 A2 | 10/1990 |
| WO | WO 94/10956 | 5/1994 |
| WO | WO 95/07673 | 3/1995 |
| WO | WO 96/20670 | 7/1996 |

\* cited by examiner

Primary Examiner—John G. Weiss
Assistant Examiner—Jamisue Webb
(74) Attorney, Agent, or Firm—Young & Thompson

(57) ABSTRACT

An absorbent article comprising a liquid-permeable casing sheet (1), a liquid-impermeable casing sheet (2) and an absorbent body (3) enclosed between the two casing sheets. The absorbent body (3) includes a liquid acquisition space (24) which consists of at least one cavity or one region of lower density than the density of an acquisition layer (19) located in said absorbent body (3) adjacent the space (24) and essentially in the same plane thereas. The acquisition layer (19) includes a material which when wetted increases in size in the thickness direction of the article (the z-direction). The article is mainly characterized in that the material in the acquisition layer (19) exhibits relatively low expansion in the plane of the article (the xy-direction) when wetted, such that the volume of the liquid-acquisition space (24) will increase by at least 100%, preferably by at least 200%, more preferably by at least 400% and most preferably by 900% when wetted.

20 Claims, 6 Drawing Sheets

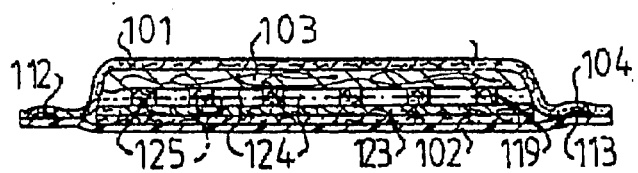
FIG.4a
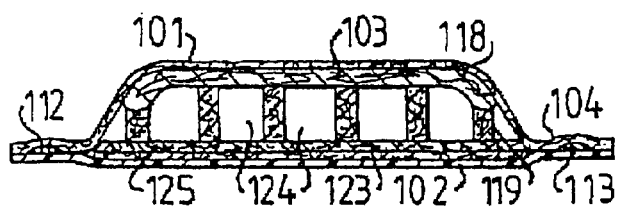
FIG.4b
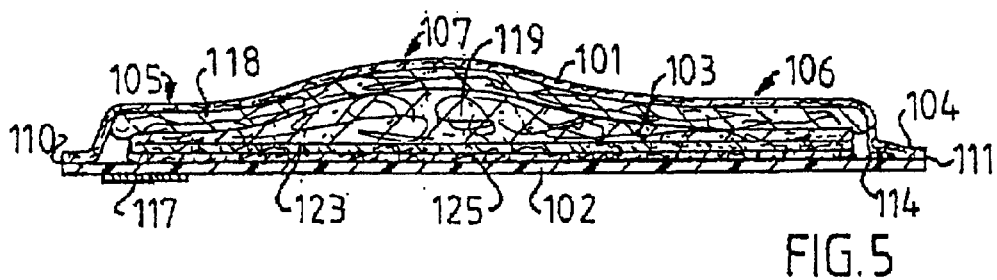
FIG.5
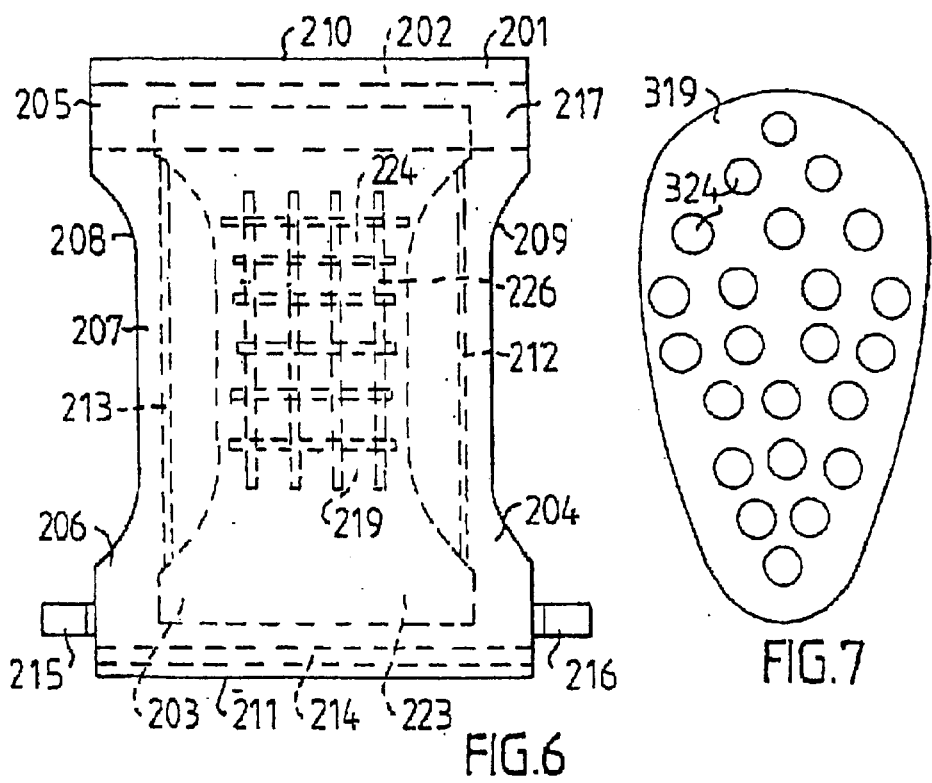
FIG.6
FIG.7

ABSORBENT BODIES IN ABSORBENT ARTICLES HAVING IMPROVED LIQUID ACQUISITION PROPERTIES

The present invention relates to an absorbent article that includes a liquid-permeable outer casing sheet mounted on a first surface of the article, a liquid-impermeable outer casing sheet mounted on a second surface of the article, and an absorbent body enclosed between said two casing sheets, wherein the absorbent body includes a liquid-reception or liquid acquisition space consisting of at least one cavity or at least one region of lower density than an acquisition layer of the absorbent body that adjoins said space essentially in the same plane thereas, and wherein the liquid-acquisition layer includes a material which when wetted increases in size in a direction (z-direction) generally perpendicular to the first surface of the article.

One problem with hitherto known absorbent articles, such as diapers, pants-type diapers or trainers, incontinence guards, sanitary napkins and like articles, that are intended to repeatedly receive and absorb body fluid excreted by a user is that the rate at which liquid is able to penetrate into the article is greatly reduced at each renewed wetting occasion. This problem is particularly apparent in diapers and incontinence guards for children and adults, since the article must be capable of receiving and absorbing a relatively large volume of liquid excreted in the course of only a few seconds. It is therewith not unusual, particularly after a first wetting of the article, that liquid which is not immediately absorbed into the article will instead flow across the surface of said article and run past the edges thereof. Such body fluid leakages are, of course, highly undesirable because, among other things, they soil and stain clothes, bed linen and mattresses, sometimes destructively.

The reason why the body fluid acquisition rate decreases with repeated wettings of the article is because the absorbent body of the article becomes temporarily saturated with body fluid within a limited area around the point at which the surface of the article is first met by the body fluid, the so-called primary wetting point. As a rule, the absorbent articles include one or more layers of hydrophilic fibres, for instance cellulose fluff pulp, and often also a powerful absorbent hydrocolloidal material, so-called superabsorbents. Liquid transport in such material is relatively slow, since it is primarily, dependent on capillary forces in those cavities present between fibres and particles in the absorbent body of the article. Liquid is transported within the hydrocolloidal materials by diffusion, which is a slower process than that generated by the capillary forces. Thus, the liquid will remain in the primary wetting region of the article for a relatively long period of time, and is then transported only gradually to surrounding parts of the absorbent body of said article.

In recent years, the problem has been accentuated by the development towards absorbent bodies that have been successively compressed to greater extents with the intention of reducing packaging volume and for transportation, storage and environmental reasons.

It is known to guide the transportation of liquid away from the primary wetting region to those parts of the absorbent body in which absorbent material that has still not been utilized is located, by providing the article with liquid transporting means in the form of compressed patterns, e.g. compressed strips, that disperse the liquid in the longitudinal direction of the article. An article that includes such compressed strips is known from PCT/SE94/00835. Liquid transportation in the article is mainly effected as a result of differences in capillary forces between the compressed strips and surrounding material. Although a certain positive effect is obtained in this way, in the form of a directed flow of liquid in the absorbent body, the rate at which the liquid is transported in the article is much too slow in relation to the rate at which body liquid is discharged onto the article. There is thus a risk that liquid will not be absorbed quickly enough and will instead run along the surface of the article and leak over the edges thereof. This risk is particularly applicable to products that are intended for urine absorption, such as diapers and incontinence guards, which must often deal with large volumes of liquid that are discharged within a relatively short time. Furthermore, heavy compression of an article makes the article stiff and imparts thereto parts that are not-readily flexible and that make the article less pliable and less liable to mould to the shape of the wearer's body when worn.

The capacity of an absorbent article to receive and retain large volumes of body liquid can also be enhanced by creating different types of liquid-receiving cavities or basins in the article.

U.S. Pat. No. 3,889,679 describes a diaper that has a plurality of circular holes disposed through the absorbent body of the diaper. However, since wetting of a diaper takes place within a limited region of the diaper, the primary wetting region, only those holes that are located nearest this region can be used to initially receive body liquid. These holes quickly fill with liquid, which is gradually drained by the surrounding absorbent material away from the holes by the suction effect generated by the capillary forces between the fibres in the absorbent material. This is a slow process, as before mentioned, and there is a considerable risk that liquid will still be left in the holes when liquid is discharged on the next wetting occasion. The absorbent material located nearest the primary wetting region of the diaper will gradually become saturated with body liquid and then lose essentially all ability to drain liquid from the holes. Another problem with this absorbent body is that it consists of a material which collapses when wetted and therewith essentially lose its three-dimensional structure. Consequently, the cavity space available in the absorbent body for acquisition of liquid is practically non-existent after a first wetting.

U.S. Pat. No. 4,560,372 describes an absorbent body that includes a resilient fibre layer and a layer of hydrophilic fibres that have been compressed, slit and then drawn apart to form openings. The absorbent body also includes 20–60% superabsorbent material. As a result of its high superabsorbent content, the material will swell in both the z-direction and in the xy-direction when wetted, i.e. the material will swell into the openings at the same time as it swells in the thickness direction of said material, wherewith the area of said openings are greatly reduced after wetting.

Swedish Patent Application No. 9304321-4 describes an absorbent body for absorbent articles such as diapers, incontinence guards and sanitary napkins that is provided with a liquid-acquisition part in the form of a drainage well that is located essentially opposite the contemplated primary wetting region of the absorbent body and that extends down into and through a liquid storage part of the absorbent body. The drainage well is in liquid communication with a liquid dispersion layer located beneath a liquid storage layer and has a greater effective mean pore size than the surrounding liquid storage part.

An absorbent body of this kind will function effectively in respect of receiving a first volume of liquid and even subsequent liquid volumes when the time between liquid discharges is sufficient to enable the well to empty of liquid between the liquid discharge occasions. The absorbent body according to Swedish Patent Application No. 9304321-4 is also dependent on capillary forces in draining liquid from the well. Consequently, the liquid-acquisition well is emptied gradually as liquid is transported from the coarser pores in the well to the finer pores in the surrounding absorbent material. There is also the risk that the well will be too small to accommodate large volumes of liquid and therewith be overfilled.

Prior publications WO 87/01914, U.S. Pat. No. 4,333,462, U.S. Pat. No. 4,333,463, U.S. Pat. No. 4.333,464, U.S. Pat. No. 4,413,996, EP 0,124,365, GB 2,156,681, U.S. Pat. No. 4,643,727 and EP 5,528,567 also describe similar products provided with liquid receiving and collecting cavities or basins.

There still remains, however, a significant demand for an absorbent article that can be wetted repeatedly at a high liquid acquisition rate, even with respect to the subsequent wetting occasions.

Our earlier invention described in our copending PCT-application WO96/20670 concerns an absorbent article which includes a li be wetted repeatedly at a high liquid acquisition rate, even with respect to the quid-permeable outer sheet disposed on a first surface of the article, a liquid-impermeable outer sheet disposed on a second surface of the article, and an absorbent body which is enclosed between the two casing sheets and which includes a body liquid receiving space comprising at least one cavity or region of lower density than the density of a part of the absorbent body located adjacent the receiving space and extending generally in the same plane thereas, the article being characterized in that the receiving space is disposed in a storage layer in the absorbent body; and in that parts of the storage layer adjacent the receiving space include a material which, when wetted, increases in volume in a direction (z-direction) generally perpendicular to the first surface of the article, whereby the size of the receiving space also increases in said direction as a result of the article being wetted.

However, the sole requirement that material of the storage layer adjacent the receiving space shall increase in volume in the z-direction does not always guarantee a substantial increase of the volume of the liquid receiving space and does, therefore, not necessarily, under all circumstances, give essentially improved liquid-acquisition properties at repeated wettings.

It is therefore an object of the present invention to achieve an absorbent article of the kind defined in the introduction having substantially improved liquid acquisition properties at repeated wettings.

There has been produced in accordance with the invention an article of the kind defined in the introduction that provides a solution to this problem. The inventive article is mainly characterized in that when wetted, the material present in the acquisition layer exhibits relatively low expansion in a direction (xy-direction) essentially parallel with the first surface of the article, such that the volume of the liquid-acquisition space will increase by at least 100%, preferably at least 200%, even more preferably 400% and most preferably at least 900% when wetted to saturation with a 0.9%-NaCl solution.

Expansion of the material in the xy-direction will not preferably be greater than that which results in a decrease in the area of the liquid-acquisition space in the xy-direction by at most 25%, preferably at most 20% and most preferably at most 10% when wetted.

Expansion of the material in the z-direction will preferably be at least 100%, preferably at least 200%, even more preferably at least 400% and most preferably at least 900%.

A storage layer is preferably disposed in liquid communication with the liquid-acquisition layer on that side of the layer that lies proximal to the liquid-impermeable outer casing sheet. The storage layer will preferably include a material having good liquid retention properties, such as cellulose fibres in combination with superabsorbent material, tissue laminates with superabsorbent material, or absorbent foam material.

According to one preferred embodiment, a dispersion layer is disposed in liquid communication with the absorption layer, either between said layer and the storage layer or between the storage layer and the liquid-impermeable outer casing sheet. The dispersion layer will preferably include a material that has good liquid dispersion properties, such as compressed cellulose pulp, a fibre mat or wadding of synthetic or natural fibres or an open-cell foam material.

There is preferably disposed between the liquid-permeable outer casing sheet and the acquisition layer a liquid transportation layer that includes a material capable of quickly accepting liquid and quickly releasing the liquid to the underlying layer. This transportation layer may be comprised of a lightly-compressed cellulose fluff layer of mechanical, thermomechanical, chemithermomechanical pulp (CTMP) chemical fibres that have been chemically stiffened or cross-linked, a fibre mat or wadding of synthetic or natural fibres or an absorbent foam material.

According to one embodiment of the invention, the liquid-acquisition space of one or more holes or regions of lower density than the density of the surrounding material in the acquisition layer extends/extend through at least a part of the thickness of the acquisition layer.

According to another embodiment, the acquisition layer is comprised of at least two separate material bodies that extend in the form of pillar-like spacer means generally perpendicular between two further material layers in the article, and together with said material layers delimit a coherent acquisition space between the material layers. According to another embodiment, the acquisition space is comprised of at least one channel-like cavity extending in the longitudinal direction of the article.

According to still another embodiment of the invention, the acquisition layer is formed by a web of material that is divided in the longitudinal direction of the web by an undulating curve, wherein the web parts are offset in relation to one another in the plane of the web, at least in the longitudinal direction thereof, such that the web parts define the acquisition space therebetween in the plane of the material web. By undulating curve is meant a curve of optional shape, such as a sinusoidal shape, a saw-toothed shape, a square-wave shape, and so on. The amplitude of the waves and their lengths can vary along the curve. The waves may extend along a straight, curved or wavy line.

A particularly suitable material for use in an inventive article for forming the acquisition layer that surrounds the liquid-acquisition space is one comprised of cellulose fibres of mechanical, thermomechanical or chemithermomechanical (CTMP)pulp and/or chemical pulp fibres that have been chemically stiffened or cross-linked, said fibres being formed into a web having a weight per unit area of 30–2000 g/m$^2$, preferably 50–1500 g/m$^2$ and more preferably 100–1000 g/m$^2$ and compressed to a density of between 0.2–1.2 g/cm$^3$, preferably 0.25–1.0 g/cm$^3$ and most preferably 0.3–0.9 g/cm$^3$. The cellulose fibres may conveniently be comprised of flash-dried fibres that have been dry-formed into a web and incorporated in the article without defibring and fluff-forming. Such a material is described in WO 94/10956. The material may be compressed to a first density of between 0.2–1.2 g/cm³ and thereafter softened mechanically to a density lower than the original density and therewith de-laminated so as to form a plurality of not completely separated thin fibre layers that have a density corresponding to the first density.

Another conceivable acquisition layer is formed of a material layer having a first thickness and including resilient material, said layer being compressed perpendicularly to a plane through the layer to a second thickness and bound in its compressed state with a binder that is soluble in body liquid, wherein binding of the material layer ceases when the layer is wetted such that the acquisition layer will return at least partially to the first thickness. Such an acquisition layer may, for instance, be formed from a compressed foam material that will expand in its thickness direction when wetted, or by a compressed fibre layer which consists at least partially of fibres that have a given resiliency in a wet state.

According to another embodiment of the invention, that proportion of the volume of the acquisition layer that is comprised of the liquid-acquisition space is greatest within the primary wetting region of the article, i.e. the region in the article that is intended to be wetted first by body liquid. The acquisition layer volume shared by the liquid-acquisition space may therewith decrease in a direction away from the primary wetting region.

Because the volume of the liquid-acquisition space in the inventive article expands in keeping with the extent to which the article is wetted by body liquid, the article is able to maintain a high liquid acquisition rate during the full length of time in which the article is worn. Distinct from earlier known articles, there is no dramatic reduction in acquisition rate with repeated wetting occasions, since a new liquid-acquisition space is constantly created. In favourable cases, the inventive article can maintain essentially the same liquid acquisition rate after a plurality of wetting occasions. In particularly favourable cases, the acquisition rate may even increase after the first wetting occasion.

In order to achieve full effect of the expanding liquid-acquisition space in an inventive absorbent body, it is essential that at least the material layer that is arranged in abutment with the side of the storage layer that lies proximal to the liquid-permeable surface of the article has a resiliency and rigidity, both in a wet and a dry state, that will prevent said material layer from collapsing and falling into the liquid-acquisition space, since otherwise a large part of the space available for further liquid accommodation would be lost.

Those cavities, regions of low density, channels or the like that together form the it liquid-acquisition space of the article will preferably not have a dimension in the plane of the acquisition layer that exceeds 35 mm and preferably does not exceed 20 mm. By this is meant that the extension of each such cavity, region of low density, channel or the like will not accommodate within its area a circle having a diameter greater than 35 mm and preferably not greater than 20 mm anywhere in the plane of the acquisition layer. Because of the flexibility of the materials, it is difficult to avoid surrounding material layers from bulging in towards the liquid acquisition space with greater dimensions than those aforesaid, therewith reducing said space. Absorbent articles shape and curve in conformity with the wearer's body in use. The material layers that lie proximal to the wearer therewith tend to curve and bulge into the acquisition space. This bulging generally increases when the material in the casing sheet is wet, and is even more pronounced when the storage layer includes large cavities. Naturally, this bulging can be reduced by using a stiffer material layer nearest the storage layer. However, the extent of the acceptable stiffness of such a material layer is determined by the requirements placed on the shapability, flexibility and user comfort of the article. The smallest functional dimension of cavities or the like in the storage layer correspond approximately to the size of a water droplet. Consequently, the size of a cavity or some corresponding space in the acquisition layer should not be so small as to enable a circle having a diameter of 3 mm or more to be enscribed inwardly of its boundary edges in the plane of the storage layer.

BRIEF DESCRIPTION OF THE DRAWINGS

The invention will now be described in more detail with reference to the Figures of the accompanying drawings, wherein

FIG. 4a is a cross-sectional view of the diaper shown in FIG. 3 taken on the line IV—IV, prior to wetting of the diaper;

FIG. 4b is a cross-sectional view of the diaper shown in FIG. 3 taken on the line IV—IV in FIG. 3 after wetting of the diaper;

FIG. 5 is a longitudinal sectional view of the diaper shown in FIG. 3 taken on the line V—V, after wetting of the diaper;

FIG. 6 illustrates a diaper having a net-forming storage layer from above;

FIG. 7 illustrates an inventive acquisition layer having a plurality of through-penetrating holes;

Figure 1:
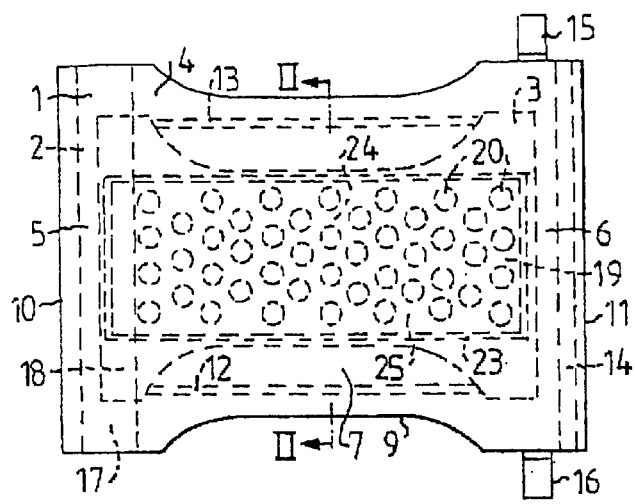
FIG. 1 illustrates a diaper according to a first embodiment of the invention from above, showing an acquisition layer formed by separate material bodies.
Figure 2A:
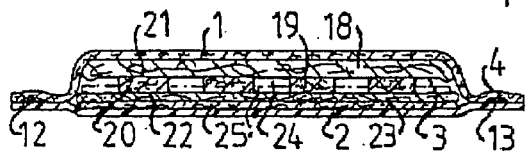
FIG. 2a is a sectional view of the diaper shown in FIG. 1 taken on the line II—II, a prior to wetting of the diaper.
Figure 2B:
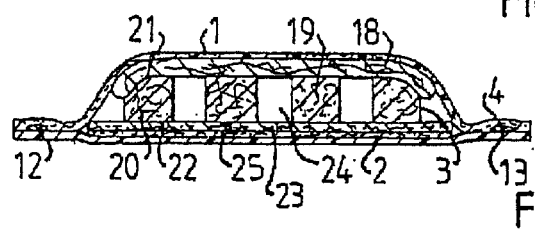
FIG. 2b is a sectional view of the diaper shown in FIG. 1 taken on the line II—II, prior to wetting of the diaper.

The diaper illustrated in FIGS. 1, 2a and 2b is seen form the side thereof that lies proximal to the wearer in use. The diaper is shown extended in a flat state and includes a first liquid-permeable casing sheet 1, e.g. made of non-woven material, perforated plastic film or net mounted on that side of the diaper which lies proximal to the wearer in use. A liquid-impermeable second casing sheet 2, comprised of plastic film, hydrophobous non-woven material or woven fabric, is placed on that side of the diaper which is intended to lie distal from the wearer in use. The two casing sheets 1, 2 enclose an absorbent body 3 and are mutually joined within parts 4 of the casing sheets 1, 2 that project out around the absorbent body 3.

The diaper is configured to surround the lower part of the wearer's trunk in a pants-like fashion when worn. To this end, the diaper includes a front part 5 which faces forwards on the wearer in use and lies over the wearer's stomach, a rear part 6 which is intended to face rearwardly on the wearer in use and lie over the wearer's bottom, and a crotch part 7 which lies between the front diaper part 5 and the rear diaper part 6 and which is intended to be placed in the crotch region between the wearer's thighs in use. The diaper has a substantially hourglass configuration, the front part 5 and the rear part 6 being broader than the crotch part 7. The diaper also includes two longitudinally extending side edges 8, 9 and a front waist edge 10 and a rear waist edge 11. The longitudinal side edges 8, 9 form the leg openings of the diaper in use, whereas the two waist edges 10, 11 together girth the waist of the wearer and form the waist opening of the diaper.

An elastic device 12, 13 is mounted along each side edge 8, 9 of the diaper. The elastic devices 12, 13 are fastened to the diaper in a stretched state and function to draw the side edges 8, 9 of the diaper together when relaxed, such as to curve the diaper to a trough-like shape. This effect of the elastic devices 12, 13 is not apparent from FIG. 1, however, since the diaper is shown in a flat state with the elastic devices 12, 13 stretched. The elastic devices 12, 13 function to hold the edges of the diaper leg-opening in tight abutment with the wearer's thighs. A further elastic device 14 is disposed along the rear waist edge 11 of the diaper, so as to bring the waist-opening defining edge in sealing abutment with the wearer's waist. Several different types of elastic devices 12–14 suitable to this end are known to the art, such as elastic threads, elastic bands, elastic non-woven, or like devices.

With the intention of enabling the diaper to be fastened together in a pants-like shape around the wearer's body in use, a fastener tab 15, 16 is provided adjacent each side edge 8, 9 in the close vicinity of the rear waist edge 11. The fastener tabs 15, 16 are intended to coact with and be fastened to a target region 17 provided on the front part 5 of the diaper. The fastener tabs 15, 16 normally have the form of tabs provided with a self-adhesive surface which is folded prior to use, with the adhesive surface lying against and protected by a tab region that has been treated with a release agent, or against the diaper itself. The target region 17 is comprised of a reinforced region of the liquid-impermeable casing sheet 2 on the front diaper part 5. The simplest way of providing this reinforcement is to laminate a strip of plastic film on the side of the liquid-impermeable casing sheet 2 that lies distal from the absorbent body 3. This reinforcement of the target area 17 enables the diaper to be opened and re-fastened without tearing the liquid-impermeable casing sheet 2.

The fastener tabs 15, 16 may, alternatively, include some type of mechanical fastener, such as one part of a burr-type fastener, a press stud, or like fastener. In this case, the target area 17 will be comprised of the corresponding part of the mechanical fastener means. It is also known to use fastener means that can almost be considered as hybrids between adhesive fasteners and mechanical fasteners. One example of such fasteners is described in EP-A-393,953. No fastener means are required for diapers that are intended to be worn as inserts in a pair of tightly fitting panties.

The absorbent body 3 includes a first layer, the transport layer 18 placed nearest inwardly of the liquid-permeable casing sheet 1. The transport layer 18 is conveniently comprised of a soft material that is able to quickly receive large volumes of liquid and which has relatively large pores or capillaries to this end. Examples of such materials are low-compressed cellulose fluff layers, in particular comprised of mechanical, thermomechanical or chemithermomechanical pulp (CTMP), chemical pulp comprised of chemically stiffened or cross-linked cellulose fibres, or fibre mats and wadding of other types of natural fibres or synthetic fibres. Mixtures of cellulose fluff pulp or other cellulose based fibres with different types of synthetic fibres may be used. Soft, perforated for open-cell foam material may also be used. The material will preferably have a low liquid dispersion ability, whereby the wet region of the layer will remain essentially restricted to the primary wetting region, even after repeated wetting of the material. The surface of the diaper that lies in contact with the wearer will therewith be felt to be dry and comfortable against the wearer's skin, even after being used for a relatively long time.

When the diaper is in use, the transport layer 18 functions to receive and transport body liquid further away from the liquid-permeable casing sheet 1 and will therefore preferably have large pores that offer the least possible resistance to the liquid flow. The transport layer 18 will also preferably be soft and comfortable against the wearer's body during the whole of its use. The properties of the material in the transport layer 18 will preferably not be changed appreciably after wetting It is also desirable that the material has a certain resiliency, so that the material will strive to return to its original state after being compressed or wrinkled in use.

When the transport layer 18 includes cellulose fibres that normally have a relatively low resiliency when wet, for instance chemical pulp, it may be suitable to mix-in other material that will enhance the wet resiliency of the material and therewith impart a certain resiliency to the first absorbent layer even when the layer is wet. Such materials are, e.g., different types of thermoplastic fibres or particles that when the layer is heated function to bind the fibres in the layer and therewith lock their relative positions such that the layer will obtain a higher tensile strength on the one hand and also greater resiliency in both a wet and a dry state on the other. The cellulose fibres can also be modified chemically by cross-linking for instance, such as to enhance their intrinsic resiliency, or by mixing the cellulose fibres with highly resilient synthetic fibres.

The transport layer 18 may also include a small quantity of so-called superabsorbents, i.e. material in the form of fibres, particles, granulates, films or the is like which are able to absorb and bind body liquid chemically in a quantity corresponding to several times the intrinsic weight of the superabsorbent while forming hydrogel.

Disposed inwardly of the transport layer 18, as seen in a direction from the liquid-permeable casing sheet 1, is a second absorbent layer 19, hereinafter referred to as the acquisition layer, which is intended to quickly receive and collect relatively large volumes of body liquid. The acquisition layer 19 consists of a plurality of cylindrical bodies 20, each having one planar surface 21 in abutment with the transport layer 18 and its other planar surface 22 in abutment with a third absorbent layer, the storage layer 23, located inwardly of the acquisition layer 19, nearest the liquid-impermeable casing sheet 2. The cylindrical bodies 20 are disposed in mutual spaced relationship and leave therebetween a coherent cavity 24 in which body liquid discharged onto the diaper can be collected. The liquid-acquisition cavity 24 may alternatively be comprised of a space of lower density and weight per unit area than peripheral material parts, and include, e.g., a porous resilient material, such as fibre wadding, an absorbent foam or like material. Material may also extend from the transport layer 18 into the cavity 24.

As will be evident from the diaper shown in FIG. 1, the main extension of the diaper lies in the xy-plane, the x-direction being defined by the transverse direction of the diaper and the y-direction being defined by the longitudinal direction of the diaper. The cylindrical bodies 20 are comprised of a material which when wetted with body liquid will expand heavily in the z-direction, i.e. in a direction perpendicular to the xy-plane, and only to a small extent in the xy-plane, such that the volume of the liquid-acquisition cavity (24) will increase by at least 100%, preferably at least 200% and more preferably by at least 500% when the material is saturated with a 0.9%-NaCl solution. Expansion of the material in the xy-direction will preferably not be greater than an extent in which the area of the cavity 24 in said xy-direction decreases by at most 25%, preferably by at most 20% and most preferably by at most 10% when wetted to saturation in accordance with the aforegoing. Expansion of the material in the z-direction will preferably be at least 100%, preferably at least 200% and most preferably at least 500% when wetted to saturation in accordance with the aforegoing.

Suitable materials for this purpose are, e.g., cellulose fibres of mechanical, thermomechanical, chemimechanical or chemithermomechanical pulp (CTMP) and/or chemical pulp fibres that have been chemically stiffened or crosslinked, said fibres being formed into a web having a weight per unit area of 30–2000 $g/m^2$, preferably 50–1500 $g/m^2$ and most preferably 100–1000 $g/m^2$, and compressed to a density of between 0.2–1.2 $g/cm^3$, preferably 0.25–1.0 $g/cm^3$ and most preferably between 0.3–0.9 $g/cm^3$. The manufacture of a particularly suitable material of this kind is described in WO 94/10956. A characteristic feature of this material is that it is produced by dry-forming flash-dried cellulose fibres to a web having a weight per unit area of 30–2000 $g/m^2$ and compressed to a density of between 0.2–1 $g/cm^3$.

Another suitable expanding material is compressed cellulose-fluff pulp (density at least 0.2 $g/cm^3$) that has been admixed with a certain amount of superabsorbent material, although less than 20% by weight superabsorbent material. The admixture of superabsorbent will namely result in an increase in the extent to which the material swells in the xy-direction, i.e. the area of the cavities 24 will decrease. However, the material used in accordance with WO 94/10956 allows a greater amount of superabsorbent to be admixed with the material, since said material swells very substantially in the z-direction, which compensates for swelling in the xy-direction.

The aforedescribed materials are produced most often in the form of relatively thin webs that have a thickness of only some few millimeters. The cylindrical bodies may therewith be formed by one or more layers of such material.

Other suitable materials with respect to the cylindrical bodies are compressed foam materials or fibre wadding which will return to their non-compressed size at least partially when wetted. When necessary, the materials may be locked in their compressed state with the aid of some form of water-soluble binder. The above examples of suitable wet-expanding materials are solely intended to illustrate the invention and shall not be considered to limit the scope thereof.

The third layer 23 of the absorbent body, hereinafter referred to as the storage layer, is comprised of a material that has a high liquid absorption and storage capacity. A suitable material in this regard is cellulose fluff pulp that has a density of between 0.08–1.0 $g/cm^3$, preferably 0.1–0.6 $g/cm^3$, in combination with 2–80%, preferably 10–50% superabsorbent, calculated on the total weight of the layer in a dry state. The superabsorbent may have the form of flakes, granules, powder or the like, and is either mixed with the cellulose fibres or applied in the form of one or more layers between fibre layers. The superabsorbent is either uniformly distributed in the storage layer 23 or at varying concentrations in the xy-direction or z-direction of the storage layer. The superabsorbent may alternatively have the form of a film.

The storage layer 23 may conceivably be comprised of a layer of essentially pure superabsorbent. Absorbent foam material, tissue laminates with superabsorbent and dry-formed, flash-dried cellulose fibre sheets according to WO 94/10956 optionally admixed with superabsorbent may also be used as storage layers.

The fourth layer 25 of the absorbent body, hereinafter referred to as the liquid dispersion layer may, in accordance with a first alternative, comprise a material of high density and highly capable of dispersing, or spreading, liquid to capillaries. Suitable materials in this respect are compressed layers of cellulose fluff pulp, tissue, absorbent foam material, or dry-formed flash-dried cellulose fibres sheets according to WO 94/10956. The dispersion layer 25 is preferably superabsorbent-free, or contains only small quantities of superabsorbent. The layer will preferably have a smaller extension in the xy-plane of the diaper than in the acquisition layer 18. The liquid dispersion layer will thereby be surrounded on all sides by a soft, body-friendly material of low liquid dispersing ability.

The dispersion layer 25 may conveniently be provided with a longitudinally extending compression pattern, such as grooves, wave patterns or the like, effective to guide the transportation of liquid in the longitudinal direction of the diaper.

According to a second alternative, the liquid dispersion layer 25 is comprised of a material that has a low resistance to liquid flow, so as to enable liquid to disperse, or spread, relatively freely along the layer. Suitable materials in this respect are a porous fibre mat or wadding of synthetic or natural fibres or an open-cell foam material.

The primary purpose of the dispersion layer 25 is to transport body liquid away from the diaper region that first receives body liquid, i.e. the primary wetting region. This results in better use of the absorbent material in the absorbent body 3. The dispersion layer 25 may either be disposed between the acquisition layer 19 and the storage layer 24, or as described above between the storage layer 24 and the liquid-impermeable outer casing sheet 2.

The cylindrical bodies 20 in the acquisition layer 19 are preferably fastened to the underlying storage sheet 23 or to the dispersion sheet 25, e.g. glued thereto, so as to prevent the cylindrical bodies 20 moving within the diaper. Alternatively, the cylindrical bodies 20 may be fastened to a separate layer, e.g. a tissue or non-woven layer, or may be fastened to the liquid-transport layer 18. Naturally, the cylindrical bodies 20 may be fastened to more than one layer.

All absorption layers 18, 19, 23, 25 in the absorbent body 3 are in direct liquid communication with one another. Thus, liquid will constantly be transported into the liquid-acquisition layer 19 of the diaper in a direction generally perpendicular to the casing sheet 1, irrespective of where liquid impinges on the liquid-permeable casing sheet 1 of said diaper.

As will be evident from FIG. 2a, the liquid-acquisition layer 19 is comparatively thin prior to the diaper having absorbed body liquid. However, the cavity 24 formed between the cylindrical bodies 20 on the diaper shown in FIG. 2a is sufficient to receive a first discharged liquid volume. The discharged body liquid hits the liquid-permeable casing sheet 1 of the diaper within a small limited region or area, the so-called primary wetting region.

The position of the primary wetting region in the diaper will vary somewhat between different users. This is due to differences in body shape on the one hand and on the sex of the user on the other hand. Male users tend to wet a diaper slightly more forwards than a female user. The position of the primary wetting region in a diaper can also vary in respect of one and the same user during use, as a result of changes in body movement and body attitudes. Thus, there is no purpose in specifically stating the position of the wetting region of the illustrated diaper. However, the primary wetting region will lie somewhere in the crotch part 7 of the diaper.

Liquid that has passed through the transport layer 18 is collected in the cavity 24 between the cylindrical bodies 20 of the acquisition layer 19 and in the fibre structure nearest around the primary wetting region of the diaper. The liquid is then spread out in the xy-plane of the diaper by the absorbent material in the dispersion layer 25.

However, part of the liquid that is collected in the cavity 24 in the acquisition layer 19 at the first wetting occasion is absorbed by the cylindrical bodies 20. Because the material in the cylindrical bodies 20 expands in the z-direction of the diaper when wetted, the expansion causes the transportation layer 18 and the storage layer 23/liquid dispersion layer 25 to be separated in the z-direction, thereby increasing the cavity 24. Thus, on the next diaper wetting occasion, the space available for instantaneous acquisition of liquid will be larger than on the first wetting occasion. The speed at which liquid enters the diaper does not therefore decrease to any appreciable extent, or may even increase with repeated wetting of the diaper absorbent body 3.

Since the cavity 24 in the liquid-acquisition layer 19 is coherent between the cylindrical bodies, liquid that penetrates through the transportation layer 18 will flow-out over a relatively large area around the primary wetting region. Liquid is absorbed into the storage layer 23 and the dispersion layer 25 relatively slowly because of the compact structure of these layers, whereby a large part of the liquid is able to run on the surface of the layer 23 that faces towards the cavity 24 and therewith spread over a considerable area prior to being absorbed by the storage layer 23 or by the cylindrical bodies 20 in the acquisition layer 19. Thus, it is not only the cylindrical bodies 20 located nearest the primary wetting region that are wetted by the liquid and swell in the z-direction, but that such expansion will also be seen to occur at a distance from the wetting region. The liquid gradually spreads further out in the diaper by virtue of liquid transportation in the dispersion layer 25, for further storage in the storage layer 23.

Figure 3:
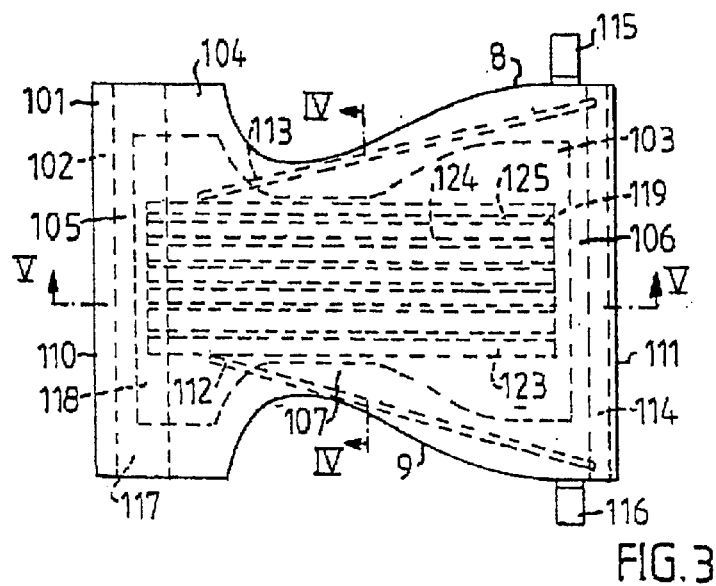
FIG. 3 illustrates a diaper according to a second embodiment of the invention from above, and shows an acquisition layer provided with longitudinally extending cavities or channels.

The diaper illustrated in FIGS. 3–5 is principally of the same construction as the diaper in FIG. 1, and includes an absorbent body 103 enclosed between a liquid-permeable casing sheet 101 and a liquid-impermeable casing sheet 102. The diaper has a front part 105, a rear part 106 and an intermediate crotch part 107 and includes two longitudinally extending side edges 108, 109, a front waist edge 110, and a rear waist edge 111. The diaper is essentially T-shaped with the cross member of the T forming the front diaper part 105 and the vertical member of the T increasing gradually in width from the diaper crotch part 107, over the rear part 106 and towards the rear waist edge 111.

Elastic devices 112, 113 are disposed along the side edges 108, 109 of the diaper in a V-shaped pattern. divergent from the front waist edge 110 towards the rear waist edge 111. A fastener tab 115, 116 is mounted on each side edge 108, 109, on the rear part 106, close to the rear waist edge 111, and a corresponding target area 117 is disposed on the outside of the liquid-impermeable casing sheet 102 at the front diaper part 106, close to the front waist edge 110.

The absorbent body 103 of the diaper includes a liquid transportation layer 118 of the same kind as that of the FIG. 1 diaper and having the same format as the size of the diaper. A liquid-acquisition layer 119 having elongated liquid-acquisition cavities or channels 124 is disposed inwardly of the transportation layer 118. As evident from the Figure, the channels 124 may extend in the longitudinal direction of the article, or alternatively in its transverse direction. The channels 124 may either be comprised of cavities punched-out in the acquisition layer 119, or alternatively an acquisition layer 119 may be comprised of a plurality of longitudinally extending, or transversely extending, strips between which elongated liquid-acquisition cavities or channels 124 are located. The strips are fastened to a storage layer 123 or to a liquid dispersion layer 125 of a kind and shape. corresponding to those of the diaper shown in FIG. 1, e.g. by gluing or in some other way.

As will best be seen from FIG. 4a, the channels 124 in the acquisition layer 119 are relatively shallow prior to wetting of the diaper. However, the volume of the channels 124 is sufficient for the diaper to receive a first liquid volume. The liquid penetrating into the diaper is able to run quickly away from the primary wetting region along the channels 124. The liquid from the channels 124 is then gradually absorbed by the acquisition layer 119, the storage layer 123 and the dispersion layer 125 respectively. Naturally, part of the liquid discharged onto the diaper and penetrating down through the transportation layer 118 will wet directly those parts of the acquisition layer 119 that are located in the primary wetting region of the diaper, these parts of said acquisition layer immediately beginning to swell in the z-direction of the diaper. Wetting of the acquisition layer 119 at a distance from the primary wetting region first takes place after a given time delay taken for the liquid to run out into the channels 124. FIG. 5 shows how liquid is spread in the longitudinal direction of the diaper as a result of varying degrees of expansion of the acquisition layer 119 (shown in sections) in the z-direction of the diaper, depending on the distance from the primary wetting region. FIG. 4b is a similar illustration showing dispersion of the liquid in the transverse direction of the diaper.

The diaper illustrated in FIG. 6 has generally the same construction as the diapers shown in FIGS. 1–5 and includes an absorbent body 203 enclosed between a liquid-permeable casing sheet 201 and a liquid-impermeable casing sheet 202. The diaper has a generally hourglass shape and includes a front part 205, a rear part 206, an intermediate narrower crotch part 207, two longitudinally extending side edges 208, 209, a front waist edge 210, and a rear waist edge 211. The elastic devices 212, 213 are disposed along the longitudinally extending side edges 208, 209 of the diaper and along the rear waist edge 211. The diaper is fastened together in a pants-like shape with the aid of two fastener tabs 215, 216 disposed on the longitudinally extending side-edges 208, 209, close to the rear waist edge 211. The fastener tabs can be fastened onto a target area 217 on the front diaper part 205, close to the front waist edge 210.

The absorbent body 203 is comprised of two layers 219, 223. The absorbent layer 219, the acquisition layer 219, located nearest the liquid-permeable casing sheet 201 is comprised of a coarse-mesh, knitted, braided or woven net 226 of material that swells in the thickness direction of the diaper, i.e. in the z-direction, when wetted. The material may, e.g., be threads, bands or strips that include a superabsorbent, gel-forming material. Another conceivable material is threads or bands coated with a polymer mixture that will ferment when wet to form a stable foam on the bands or threads. Disposed beneath the acquisition layer 219, seen in a direction away from the liquid-permeable casing sheet 201, is a storage layer 223 of the same kind as that described with reference to the diapers shown in FIGS. 1–5. Naturally, the diaper illustrated in FIG. 6 may also be provided with a soft, coarse-pore liquid-acquisition transportation layer between the liquid-permeable casing sheet 201 and the storage sheet 219, if so desired. Similarly, a liquid dispersion layer may be disposed in a manner corresponding to that described with reference to FIGS. 1–5.

FIG. 7 illustrates an alternative embodiment of a liquid-acquisition layer 319 comprised of a material that can swell in the z-direction. The acquisition layer 319 includes a plurality of through-penetrating circular holes 324 that function as liquid collecting reservoirs. The acquisition layer 319 is intended to be used as the sole absorption layer, or together with further absorption layers, such as liquid transportation layers, storage layers and/or dispersion layers in an absorbent article, such as a diaper, a sanitary napkin, an incontinence guard or like article. Because the acquisition layer swells in the z-direction, i.e. in its thickness direction, when wetted, the volume of the holes 324 will increase and therewith also their liquid accommodating capacity.

The highest proportion of cavities 324 in the acquisition layer 319 are located in the region that is intended to be placed in the primary wetting region of the absorbent article. Since the holes 324 are not mutually connected, no liquid is unable to flow freely between the holes but is dispersed in the xy-plane of the acquisition layer 319 through capillary transportation in the absorbent material located between the holes 324. Consequently, there is no apparent reason for providing holes 324 at too far a distance from the primary wetting region.

Figure 8:
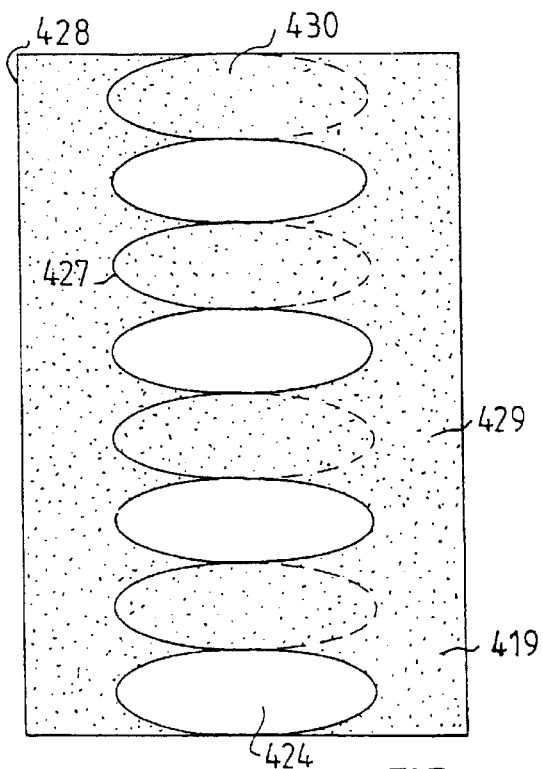
FIG. 8 illustrates an acquisition layer having centrally disposed openings alternating with overlapping material regions.

FIG. 8 illustrates a further embodiment of an acquisition layer 419 for use in absorbent articles. The acquisition layer according to FIG. 8 is formed from a web of material that is cut into two pieces longitudinally along a sinusoidal curve 427, whereafter the two web halves 428, 429 have been offset relative to one another in the longitudinal direction of the web through a distance corresponding to one-half wave length. There is thus formed in the longitudinally extending centre part of the web holes 424 that alternative with overlapping web-parts 430. As in the earlier described embodiments, the acquisition layer 419 is comprised of a material which swells in the thickness direction of the material, i.e. in the z-direction, when wetted.

Figure 9:
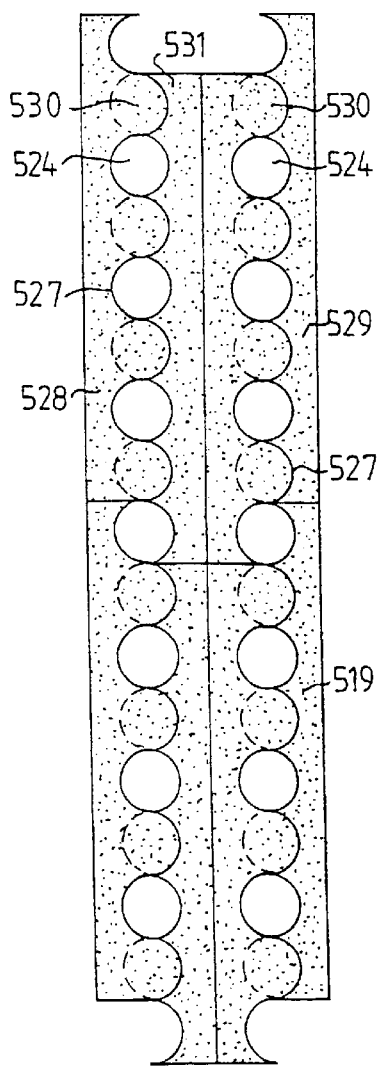
FIG. 9 illustrates a web of material for producing an acquisition layer.

Shown in FIG. 9 is an example of another web material provided with holes 524 and formed by first cutting the web 519 into two parts longitudinally in a curved pattern, whereafter the separated parts of the web have been offset longitudinally so as to produce a repetitive pattern of openings 524 and overlapping parts 530 in the web. The web 519 shown in FIG. 9 has been cut longitudinally along two generally sinusoidal curves 527. Subsequent to offsetting the edge parts 528, 529 of the web in relation to its centre part 531, there are obtained two longitudinally extending rows of holes 524 with intermediate overlapping parts 530.

Naturally, the principle can be used to provide any desired number of rows of openings in a web of material. In this regard, the number of hole rows is determined by the number of curve-shaped cuts made in the web.

Figure 10:
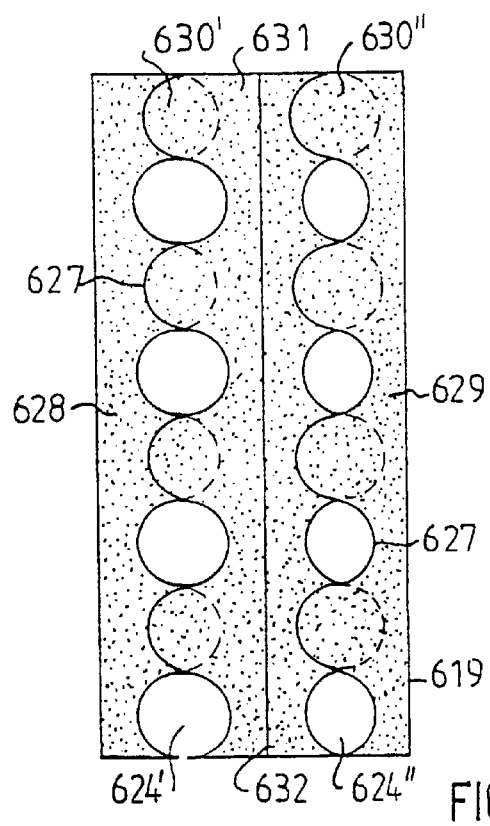
FIG. 10 illustrates an acquisition layer having two rows of holes of mutually different sizes.

The web 619 shown in FIG. 10 has been cut longitudinally in the same way as the web 519 in FIG. 9. One edge-part 628 of the web 619 has then been displaced longitudinally and transversely away from the longitudinal centre line 632 of the web 619. The other edge part 629 has been displaced both longitudinally and transversely in towards the longitudinal centre line 632 of the web 619. This enables the size of the holes 624', 624" and the size of the overlapping parts 630', 630" to be adjusted. The size of the holes 624" can be reduced, by displacing an edge part 629 towards the longitudinal centre line 632 of the web 619, while obtaining a larger overlap 630" between the web parts at the same time. the size of the hole 624' is increased in a corresponding manner, by displacing the edge part 628 of the web 619 away from the centre line 632.

Figure 11:
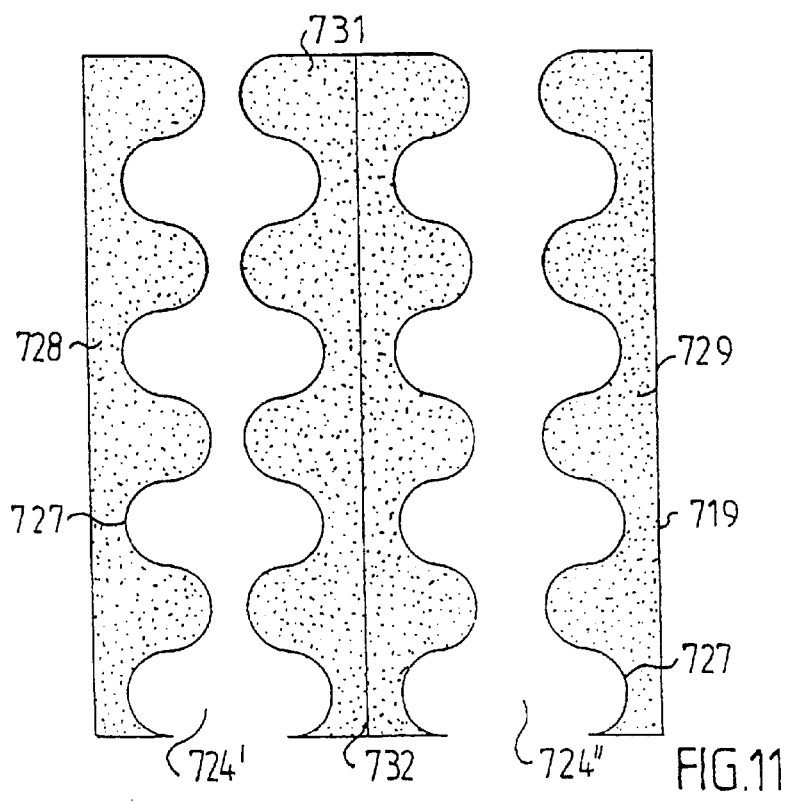
FIG. 11 illustrates an acquisition layer having undulating, groove-like cavities.

FIG. 11 illustrates the manner in which coherent, longitudinally extending openings can be obtained between parts of a material web 719 that has been cut apart along generally sinusoidal curves 727. The web parts 728, 729, 731 in FIG. 11 are mutually displaced both in the longitudinal and in the transversal direction of the web 719, by moving the cut edge parts 728, 729 laterally away from the longitudinal centre line 732 of the web 719. The width of the coherent openings 724', 724" between two web parts is determined by the distance at which the web parts are separated. FIG. 11 shows two examples of openings of mutually different widths 724', 724". Naturally, the web 719 may be provided with any number of coherent openings of the aforedescribed kind.

The web parts may be placed in the article with the curved cuts or slits either in the longitudinal direction of the article or in its transverse direction. Other curve shapes than sinusoidal shapes may be chosen, such as saw-toothed shapes or square-wave shapes.

Varying sizes can be obtained with waves that have different amplitudes along the curve, e.g. such that the holes located in the wetting region will be larger than the holes located outside said region. Waves of varying wave lengths can also be chosen wherewith a varying overlap is obtained between the holes at a given offset between the web parts.

EXAMPLE

Samples measuring 5×5 cm were punched from sample materials comprising:

A) DFR (dry-formed reel pulp), i.e. a dry-formed pulp sheet of flash-dried cellulose fibres of CTMP (according to WO 94/10956); weight per unit area 300 g/m².

B) DFR according to the above admixed with 20% by weight superabsorbent (Salsorb CL10).

C) Chemical cellulose fluff pulp admixed with 48% by weight superabsorbent (IM 7100), weight per unit area 500 g/m².

D) Chemical cellulose fluff pulp admixed with 30% by weight superabsorbent (IM 7100), weight per unit area 300 g/m².

Four circular holes measuring 10 mm in diameter were punched out of each sample.

The samples were weighed in a dry state and their thickness measured with a measurement tool of 45×45 mm at a pressure of 2.5N.

The samples were placed on a dense net material (tea bag-like material) and were allowed to swell freely in a basin containing 0.9%-NaCl solution.

The samples were then removed from the basin and allowed to drip for about 30 seconds, whereafter the wet thickness was measured and the sample weighed.

The difference between the wet and the dry thickness constitutes the swellability of the material in its z-direction.

The following results were obtained:

TABLE 1

Swellability in z-direction.

| Sample | Dry weight g | Wet weight g | Dry thickness mm | Wet thickness mm | Increase % |
|---|---|---|---|---|---|
| A | 0.75 | 17.71 | 0.42 | 5.57 | 1226 |
| B | 1.17 | 32.50 | 0.96 | 8.51 | 786 |
| C | 2.30 | 77.57 | 8.96 | 22.19 | 148 |
| D | 1.19 | 37.27 | 5.18 | 12.21 | 136 |

The measuring results constitute the mean value of four measurements.

With the intention of measuring swelling in the xy-direction and the influence of swelling on the size of the holes, an image analysis was carried out with the aid of the programmes Image Grabber and Optilab as follows:

Samples according to the above were placed in a small glass bowl.

A dark paper was placed on the light table of the image analysis apparatus and glass bowl and sample were placed on the paper.

The image Grabber programme was opened and the camera focused. Four images were taken of the dry sample directly from above, one for each hole.

A 0.9%-NaCl solution was poured carefully into the bowl and the sample allowed to absorb liquid freely for twenty minutes.

Excess liquid was removed carefully with a pipette.

Four images were taken directly from above the wet sample, one for each hole.

Figure 12A:
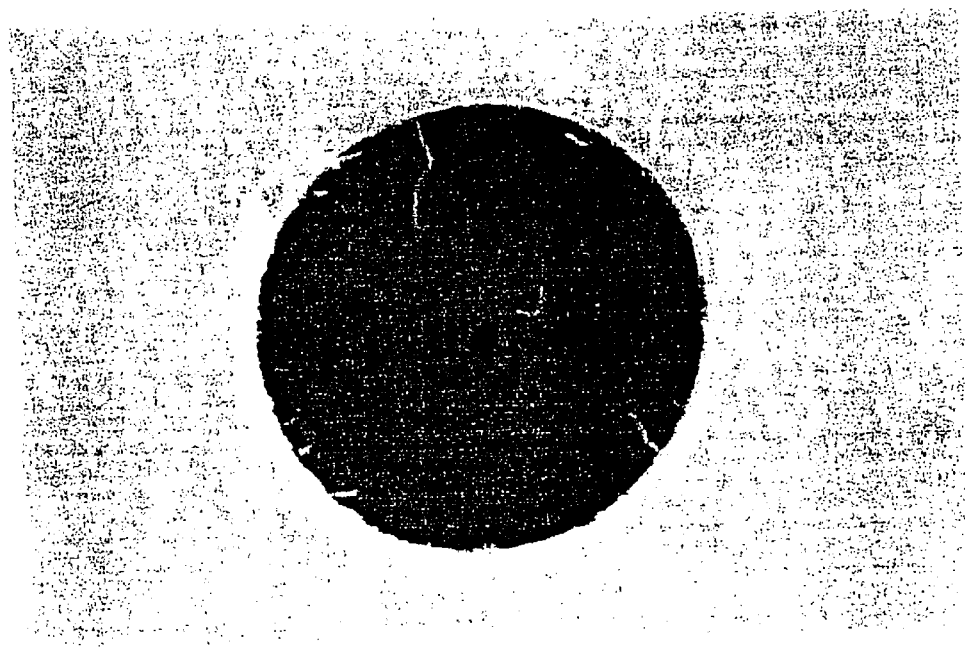
FIGS. 12a and b are larger views of a hole and surrounding parts of a respective dry and wet sample of a first material.
Figure 12B:
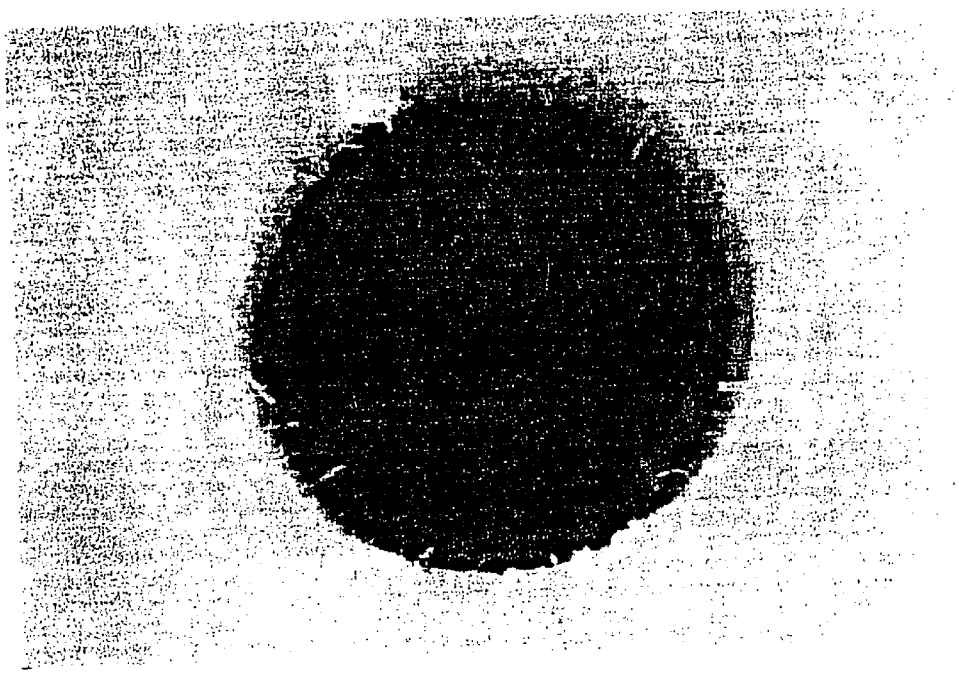

FIGS. 12a and b illustrate a hole with surrounding parts of a dry and a wet sample piece of sample A respectively.

Figure 13A:
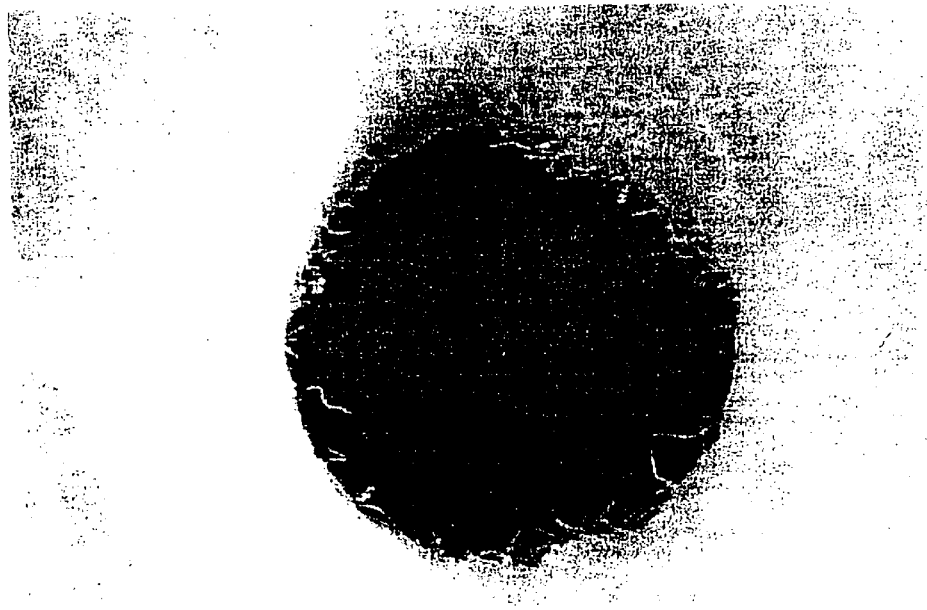
FIGS. 13a and b are enlarged views of a hole with surrounding parts of a respective dry and wet sample of a second material.

FIGS. 13a and b illustrate a hole with surrounding parts of a dry and a wet sample Piece of sample C respectively.

As evident from the images, the hole in sample piece A has substantially retained its area after wetting, whereas the hole area of sample piece C has decreased substantially.

The size (the area) of the hole was measured in the following way:

A dry scale image was taken by placing a vernier caliper set at 10.0 mm on the dry an sample, whereafter an image was taken in the image Grabber.

A wet scale image was taken by placing a vernier caliper set to 10.0 mm on the wet sample and thereafter taking an image in the image Grabber.

The Optilab programme (Graftek) was opened for calibration of the scale. A line was drawn on the calibre image, which was calibrated to 10.0 mm.

Each hole to be measured was calibrated against the scale image of respective samples.

Figure 13B:
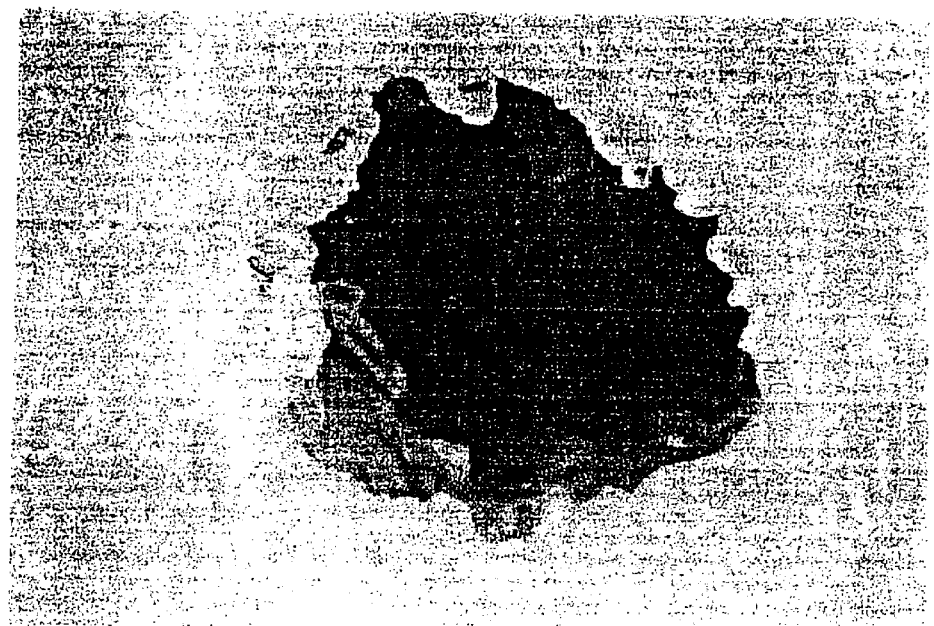

The grey scale at the edge of the hole was measured, i.e. the distinguishing line between greyish and grey (FIG. 13b), wherein black is the hole, grey is the superabsorbent and the greyish the colour of the pulp.

The hole area in mm was marked and the result printed out.

The following results were obtained:

TABLE 2

Change of hole area and hole volume when wetting.

| Sample | Hole area dry $mm^2$ | Hole area wet $mm^2$ | Hole vol. dry $mm^3$ | Hole vol. wet $mm^3$ | Change hole vol. % |
|---|---|---|---|---|---|
| A | 7.53 | 7.31 | 3.16 | 40.71 | 1188 |
| B | 7.50 | 4.98 | 7.20 | 42.38 | 489 |
| C | 6.99 | 2.86 | 62.63 | 63.46 | 1 |
| D | 7.22 | 4.41 | 37.42 | 53.84 | 44 |

The measuring results constitute the mean value of four measurements. The hole volume was calculated as the product of hole area and sample thickness (Table 1).

The results obtained for the samples C and D show clearly that the requirement that the material of the acquisition layer shall increase in size in the z-direction is not enough to ensure a substantial increase of the volume of the liquid-acquisition space. In fact, the sample C having an increase in the z-direction of 148 % gives a volume increase of only 1%. The sample D is only marginally better. Thus, the requirement of the present invention that the material of the acquisition layer also must show a relatively low expansion in the xy-direction when wetted is essential.

Although the invention has been described in the aforegoing generally with reference to diapers, it will be understood that the invention can be applied to all types of absorbent articles that are intended to absorb body liquid. Examples of such articles are diapers and incontinence guards for children and adults, sanitary napkins, panty liners, bed protectors, seat protectors, wound dressings and like articles.

It will also be understood that the invention is not limited to the described shapes and sizes of holes, channels and swellable bodies, and that a number of further embodiments are conceivable. For instance, holes disposed in a liquid-acquisition layer may have any suitable form or size. It is, of course, also possible to combine holes and channels of different shapes and sizes in one and the same article. Swellable bodies disposed as "columns" in a coherent cavity may also vary in size and shape and are not restricted to the aforedescribed cylindrical bodies. As before mentioned, the liquid-acquisition cavities may also be comprised of a space whose density and weight per unit area are lower than the density and weight per unit area of the surrounding acquisition layer and may, for instance, include a porous, resilient material such as fibre wadding, an absorbent foam material or the like.

An absorbent body may also include more than one acquisition layer. In this regard, further acquisition layers may be of the same kind as the first acquisition layer or may differ therefrom by virtue of material selection or construction.

What is claimed is:

1. In an absorbent article that includes a liquid permeable outer casing sheet (1) disposed at a first surface on the article, a liquid-impermeable casing sheet (2) disposed at a second surface on the article, an absorbent body (3) enclosed between the two casing sheets, an acquisition layer (19), that includes a material which when wetted increases in size in a direction (z-direction) perpendicular to the first surface of said article, and a liquid acquisition space (24) that comprises at least one region of lower density than said acquisition layer (19) and that lies in a same plane as said acquisition layer; the improvement wherein the material in the acquisition layer (19) has, when wetted, lower expansion in a direction (xy-direction) parallel to the first surface of the article than in said perpendicular direction, such that the volume of the liquid acquisition space (24) will increase by at least 100% when said acquisition layer (19) is wetted to saturation with a 0.9%-NaCl solution.

2. An absorbent article according to claim 1, characterized in that the volume of the liquid-acquisition space (24) increases by at least 200%.

3. An absorbent article according to claim 1, characterized in that expansion of the material in the xy-direction is not greater than to result in a reduction of area of the liquid-acquisition space (24) in the xy-direction by at most 25% when wetted to saturation with a 0.9%-NaCl solution.

4. An absorbent article according to claim 1, characterized in that the expansion of the material in the z-direction is at least 100% when wetted to saturation with a 0.9%-NaCl solution.

5. An absorbent article according to claim 1, characterized in that a storage layer (23) is arranged in liquid communication with the acquisition layer (19) on a side of said acquisition layer lying proximal to the liquid-impermeable casing sheet (2).

6. An absorbent article according to claim 5, characterized in that the storage layer (23) includes a material that has good liquid-retaining properties.

7. An absorbent article according to claim 5, characterized in that a liquid dispersion layer (25) is arranged in liquid communication with the acquisition layer (19), either between said acquisition layer and the storage layer (23) or between the storage layer and the liquid-impermeable casing sheet (2).

8. An absorbent article according to claim 7, characterized in that the dispersion layer includes a material that possesses good liquid dispersion properties.

9. An absorbent article according to claim 1, characterized by a liquid transportation layer (18) disposed between the liquid-permeable casing sheet (1) and the acquisition layer (19).

10. An absorbent article according to claim 9, characterized in that the transportation layer (18) includes a material that is capable of quickly receiving liquid and releasing the liquid to underlying layers.

11. An absorbent article according to claim 1, characterized in that the liquid-acquisition space (24) is comprised of one or more holes that extend through at least parts of the thickness of the acquisition layer (19), or regions of lower density than the surrounding material (20, 125) in the acquisition layer (19).

12. An absorbent article according to claim 1, characterized in that the acquisition layer (19) is comprised of at least two separate material bodies (20) that extend as pillar-like spacing devices generally perpendicularly between a liquid transport layer (18) and a liquid storage layer (23) in the article and define together with said liquid transport layer (18) and said liquid storage layer (23) a coherent liquid-acquisition space (24) between said liquid transport layer (18) and said liquid storage layer (23).

13. An absorbent article according to claim 1, characterized in that the liquid-acquisition space (124) is comprised of at least one channel (124) that extends in the longitudinal direction of the article.

14. An absorbent article according to claim 1, characterized in that the proportion of the volume of said acquisition layer (19) that is comprised of the liquid acquisition space (24) is greatest within the region of the article that is intended to be wetted first by body liquid.

15. An absorbent article according to claim 1, characterized in that the acquisition layer (19) is comprised of cellulose fibres of mechanical, thermomechanical, chemimechanical or chemithermomechanical pulp (CTMP) and/or chemical pulp fibres that have been chemically stiffened or cross-linked, said fibres having been formed into a web having a weight per unit area of 30–2000 $g/m^2$, and compressed to a density of between 0.2–1.2 $g/cm^3$.

16. An absorbent article according to claim 15, characterized in that the acquisition layer (19) is comprised of an air-laid web of cellulose fibers that has been compressed into a dry-formed sheet that has a first density of between 0.2–1.2 $g/cm^3$ and which has then been softened mechanically to a second density that is lower than the original density and therewith delaminated, thereby to form a plurality of not fully separated thin fibre layers that have a density corresponding to the first density.

17. An absorbent article according to claim 15, characterized in that the cellulose fibres are comprised of flash-dried fibres that have been dry-formed into a web and incorporated in the article without defibration and fluff-forming.

18. An absorbent article according to claim 1, characterized in that the acquisition layer (19) is comprised of a material layer having a first thickness and including resilient material, said material layer having been compressed perpendicular to a plane through the layer to a second thickness and bound in its compressed state with a binder that is dissolvable in body liquid, wherein said binding of the material layer ceases when the layer is wetted and the acquisition layer (19) returns at least partially to said first thickness.

19. An absorbent article according to claim 18, characterized in that the acquisition layer (19) is comprised of a compressed fibre layer that comprises at least partially fibres having resiliency in a wet state.

20. An absorbent article according to claim 18, characterized in that said acquisition layer (19) is comprised of a compressed foam material that will expand in its thickness direction when wetted.

* * * * *